United States Patent
Bissinger et al.

(12) 
(10) Patent No.: US 6,395,801 B1
(45) Date of Patent: *May 28, 2002

(54) IMPRESSION COMPOSITIONS COMPRISING TRIGLYCERIDES

(75) Inventors: Peter Bissinger, Königsbrunn; Günther Lechner, Wörthsee; Erich Wanek, Kaufering, all of (DE)

(73) Assignee: Thera Patent GmbH & Co KG Gesellschaft fur Industrielle Schutzrechte, Seefeld (DE)

(*) Notice: Subject to any disclaimer, the term of this patent is extended or adjusted under 35 U.S.C. 154(b) by 0 days.

This patent is subject to a terminal disclaimer.

(21) Appl. No.: 09/544,116

(22) Filed: Apr. 6, 2000

Related U.S. Application Data

(62) Division of application No. 09/044,120, filed on Mar. 19, 1998, now Pat. No. 6,127,449.

(30) Foreign Application Priority Data

Mar. 19, 1997 (DE) .......................... 197 11 514

(51) Int. Cl.⁷ ............................ A61K 6/10; C08K 5/103
(52) U.S. Cl. ....................... 523/109; 433/214; 524/313; 524/612
(58) Field of Search ........................... 523/109; 524/313, 524/612; 433/214

(56) References Cited

U.S. PATENT DOCUMENTS

| | | | |
|---|---|---|---|
| 5,321,054 A | 6/1994 | Pasini | 523/109 |
| 5,348,474 A | 9/1994 | Pasini | 433/214 |
| 5,569,691 A | * 10/1996 | Guggenberger et al. | 524/261 |
| 6,127,449 A | * 10/2000 | Bissinger et al. | 523/109 |

FOREIGN PATENT DOCUMENTS

| | | |
|---|---|---|
| DE | 4306997 A1 | 9/1994 |
| DE | 3805482 C2 | 4/1995 |
| EP | 0566221 A2 | 10/1993 |

OTHER PUBLICATIONS

Causton et al. "*J. Dent. Res.*" vol. 51, No. 4, pp. 889–896, (1972).

Encyclopedia of Industrial Chemistry, Ullman, 5$^{th}$ Edition, vol. A10, pp. 174, 175 and 177.

* cited by examiner

*Primary Examiner*—Peter Szekely
(74) *Attorney, Agent, or Firm*—Birch Stewart Kolasch & Birch LLP

(57) ABSTRACT

The invention relates to impression compositions based on vulcanizable polyether materials, which are characterized in that the ready-mixed pastes comprise a) approx. 30 to 70 wt. % of aziridino-polyether,
b) approx. 5 to 20 wt. % of a triacyl glyceride of non-animal origin which has a stearoyl content of ≧70 wt. %, based on the acyl content of the triacyl glyceride, or, in the case of a lower stearoyl content and if this adversely influences the storage stability of the impression composition, has been esterified in itself beforehand, and
c) approx. 10 to 65 wt. % of customary catalysts, auxiliaries and additives, in each case based on the total weight of the composition.

The impression compositions are distinguished by consistently good mechanical properties of the polymerized materials, have a comparatively low proportion of aziridino-polyether, which has a favorable effect on their preparation costs, and can easily be mixed. During storage of the compositions over long periods of time, no noticeable increase in viscosity occurs, even at elevated temperatures.

14 Claims, No Drawings

IMPRESSION COMPOSITIONS COMPRISING TRIGLYCERIDES

This application is a divisional of application Ser. No. 09/044,120, filed on Mar. 19, 1998, now U.S. Pat. No. 6,127,449 the entire contents of which are hereby incorporated by reference.

The present invention relates to rubber-elastic impression or duplicating compositions which are based on vulcanizable polyether materials and are used, in particular, in the dental field, and also in orthopedics. In particular, the present invention describes vulcanizable polyether pastes with aziridino end groups, addition-crosslinking polyether silicone pastes with H—Si groups, and polyether acrylate and methacrylate pastes which can be vulcanized by free radicals, for the production of accurate impressions of jaws with teeth, some teeth or no teeth and of gypsum models.

DE-B-17 45 810 discloses impression compositions of polyether materials with aziridino end groups. DE-A1-37 41 575 and DE-A1-38 38 587 disclose impression compositions based on polyether materials with alkenyl groups and polyorganosiloxane radicals containing H—Si groups, which polymerize under the action of platinum catalysts. EP-A2-0 173 085 discloses impression compositions of polyether materials with acrylate and methacrylate groups which, after irradiation with light of suitable wavelength, polymerize—under initiation by the dissociation of a photoinitiator. DE-A1-43 06 997 furthermore discloses impression compositions based on polyether materials which are hydrophilized by additives. These materials have a good capacity for flowing on hydrophilic oral surfaces and therefore have a higher impression sharpness for these applications than other known impression compositions, e.g. based on conventional hydrophobic silicones.

To simplify processing of these impression compositions, thixotropic agents, such as highly disperse fillers, e.g. described in DE-A1-43 21 257, or fats of various origins, e.g. described in DE-A1-43 06 997, are added to them. DE-A1-195 05 896 furthermore describes the addition of hydrogenated beef tallow to aziridine-free impression materials. It is known that these thixotropic agents should not exceed a proportion by weight of approx. 10% in polyether materials with aziridino end groups, so that the mechanical properties of the cured impression composition is not adversely influenced. This means that the proportion of aziridino-containing polyethers of such impression compositions must lie in the range from 50 to 70 per cent by weight, which therefore leads substantially to these materials becoming more expensive. Another disadvantage of admixing the thixotropic agents used to date is that the viscosity of polyether pastes comprising such thixotropic agents increases constantly in the course of storage, and the usable life of these materials is therefore adversely restricted. Pastes without these thixotropic agents show no tendency to thicken.

The object of the present invention is to provide impression compositions which are based on polyethers and comprise thixotropic agents, which can be admixed in amounts of >10 percent by weight without the mechanical properties of the cured compositions being adversely influenced. Furthermore, the impression compositions prepared with these thixotropic agents should show the lowest possible increase in viscosity with increasing storage time.

The object is achieved by impression compositions which are characterized in that they comprise a) approx. 30 to 70 wt. % of aziridino-polyether,
b) approx. 5 to 20 wt. % of a triacyl glyceride of non-animal origin which has a stearoyl content of >70 wt. %, based on the acyl content of the triacyl glyceride, or, in the case of a lower stearoyl content and if this adversely influences the storage stability of the impression composition, has been esterified in itself beforehand, and
c) approx. 10 to 65 wt. % of customary catalysts, auxiliaries and additives, in each case based on the total weight of the ready-mixed composition.

The impression compositions according to the invention preferably comprise 30 to 40 wt. % of component a), 5 to 20 wt. % of component b) and 40 to 65 wt. % of component c), in each case based on the total weight of the ready-mixed composition.

Impression compositions of this combination are distinguished, compared with the polyether impression materials which are known to date and are based on aziridine, by consistently good mechanical properties of the completely vulcanized and polymerized materials (see examples 1 and 4 and table 1), with a significantly lower content of aziridino-polyether at the same time. As a result, the compositions according to the invention can be produced considerably less expensively.

In addition, the impression compositions can be mixed more easily by the use of triacyl glycerides of non-animal origin according to component b), and therefore allow a shorter production time. Surprisingly, it has been found that by the addition of the triacyl glycerides described, the compositions according to the invention show no substantial increase in the viscosity over a period of up to 24 months during storage, even at elevated temperature (examples 1 to 4; and table 1). However, this effect can preferably be achieved with those triacyl glycerides of non-animal origin in which the stearoyl content is greater than or equal to 70 wt. %, based on the acyl content of the triacyl glyceride. If triacyl glycerides in which the stearoyl content is less than 70 wt. %, based on the acyl content of the triacyl glyceride, are used in the compositions according to the invention, a thickening is sometimes observed during storage, especially at elevated temperature (comparison examples 1 to 4; and table 1). But if such triacyl glycerides are pretreated by interesterification (esterification in themselves), as described in preparation example 2, before being admixed to the impression composition, the polyether impression compositions produced therefrom surprisingly show no substantial increase in the viscosity during storage at elevated temperature (example 2 and table 1). However, triacyl glycerides in which the stearoyl content is <70 wt. % can also be employed if the storage stability of the impression composition is not adversely influenced as a result.

The esterification in the fat itself can be carried out in principle by stirring the fat with a strong base and subsequent neutralization (in this context, see also "Ullmann's Encyclopaedia of Industrial Chemistry", 5$^{th}$ ed., volume A10, p. 209).

A large number of triacyl glycerides can therefore be used for preparation of the compositions according to the invention, such as e.g. avocado oil, cottonseed oil, groundnut oil, cacao butter, pumpkin seed oil, linseed oil, maize germ oil, olive oil, palm oil, rice oil, rapeseed oils, safflower oil, sesame oil, soya oil, sunflower oil, grapeseed oil, wheatgerm oil, borneo tallow, fulwa tallow, hemp oil, illipé butter, lupin-oil, candlenut oil, kapok oil, katiau fat, kenaf seed oil, kekuna oil, poppy oil, mowrah butter, okra oil, perilla oil, sal butter, shea butter and tung oil, if these fats have been hydrogenated before their use. Hydrogenated fats which are regarded as suitable are those which have an iodine number (measured in accordance with the standard DGF C-V 11b) of less than 20. Particularly preferred fats are those which have an iodine number of less than 5. Fat hydrogenations are carried out, for example, as described in "Ullmanns Enzyklopädie der industriellen Chemie [Ullmann's Encyclopaedia of Industrial Chemistry]", 4th ed., volume 11, p. 469. Mixtures of these naturally occurring fats as well as synthetically produced fats, such as e.g. Softisan 154 or Dynasan 118 (Hüls) can also be used. The preparation of such synthetic triacyl glycerides is relatively simple for the expert and can be carried out, for example, from glycerol and the corresponding fatty acid methyl esters. Such esterification reactions are described, inter alia, in "Houben-Weyl, Methoden der Organischen Chemie [Methods of Organic Chemistry]", vol. E5/part 1, p. 659 et seq.

Preferred triacyl glycerides correspond to the following formula

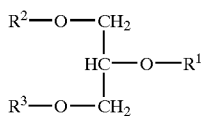

in which $R^1$, $R^2$ and $R^3$ independently of one another denote $C_{11}H_{23}CO$, $C_{13}H_{27}CO$, $C_{15}H_{31}CO$ or $C_{17}H_{35}CO$, the proportion of $C_{17}H_{35}CO$ (stearoyl) being $\geq 70$ wt. %, based on the acyl content of the triacyl glyceride. Mixtures of such triacyl glycerides are also possible. If the proportion of $C_{17}H_{35}CO$ is less than 70 wt. %, the content of this radical must be distributed randomly over $R^1$, $R^2$ and $R^3$, so that the storage stability of the impression composition is not adversely influenced. Triacyl glycerides of natural origin which are esterified in themselves and synthetically prepared triacyl glycerides meet the condition of random distribution intrinsically.

Polyether materials according to component a) which are suitable for the use according to the invention are known to the expert. The polyether materials described in DE-B-17 45 810 are particularly preferred for the purpose according to the invention.

Preferred catalysts according to component c) are described in DE-A1-25 15 593, and suitable retardants are described in EP-A1-0 110 429. Other suitable catalysts are e.g. sulphonium salts, for example those which are described in U.S. Pat. No. 4,167,618. The disclosure content of the publications mentioned which is referred to is to be expressly included here.

Customary auxiliaries and additives according to component c) are stabilizers, plasticizers, pigments and fillers. Examples of such auxiliaries and additives are described, inter alia, in DE-A-17 48 510.

To prevent premature curing of the impression compositions, the polyether materials on the one hand and the catalysts on the other hand must be kept separate from one another until used. Preferably, the two components are present in the form of pastes. In a preferred embodiment, the base components and the catalyst are present in paste form and spatially separate from one another, the base component comprising i) 30 to 75 wt. % aziridino-polyether, ii) 5 to 25 wt. % of a triacyl glyceride of non-animal origin which has a stearoyl content of $\geq 70$ wt. %, based on the acyl content of the triacyl glyceride, or, in the case of a lower stearoyl content and if this adversely influences the storage stability of the impression composition, has been esterified in itself beforehand, and iii) 0 to 65 wt. % of customary auxiliaries and additives, and the catalyst component comprising iv) 10 to 60 wt. % of a customary catalyst, v) 0 to 25 wt. % of a triacyl glyceride according to component ii) and vi) 15 to 90 wt. % of customary auxiliaries and additives, the wt. % data in each case being based on the total weight of the base paste and catalyst paste respectively.

To improve the mixing properties with the polymerization catalyst of the other paste, which catalyst is dissolved in the solvent or plasticizer or kept in suspension by means of suspending agents or kept in emulsion by means of emulsifiers, the vulcanizable polyether materials of the one paste can comprise the same or chemically similar plasticizers or solvents.

The use of solutions of the crosslinking agent in suitable plasticizers, solvents or plasticizer mixtures is expedient; in this manner, not only are extreme mixing ratios avoided, but solid initiators are also dissolved.

Customary plasticizers are often readily compatible with the polyether materials. Their use is advisable not only for economic reasons, but also to improve the properties, in particular to avoid or reduce crystallization. Plasticizers which are suitable are, for example, phthalic acid esters, glycol derivatives and polymeric plasticizers, sorbitan esters etc. Customary and suitable plasticizers are described, for example, in Polyethers, part I, edited by Norman G. Gaylord, Interscience Publishers (1963). The properties of the end products can be varied widely by the choice of a suitable starting material, so that the mechanical values of the end products can be established virtually as required. Nevertheless, the addition of relatively large amounts of plasticizer and/or other customary additives can influence the absorption of water, swelling and change in dimensions to a degree such that the impression cannot be used.

EXAMPLES

Preparation Example 1

Preparation of a Catalyst Paste 32.7 g of a sulphonium salt which has been obtained according to example 27 of DE-A1-25 15 593, 32.2 g acetyl-tributyl citrate, 5.8 g of a block copolymer surfactant of propylene oxide and ethylene oxide having an average molecular weight of 6,500, 19.1 g pyrogenic silicic acid, 9.5 g kieselguhr and 0.7 g pigments are kneaded to give a total of 100 g of a paste. This is used as paste B in the following examples.

Comparison Example 1

57.9 g of an aziridino-polyether which has been obtained according to example 12 of DE-B 17 45 810 are mixed with 11.6 g dibenzyltoluene, 11.6 g hydrogenated palm oil and 16.3 g kieselguhr. After addition of 2.6 g of a mixture of retardant, coloured pigment and aroma, 100 g of a paste VA1 are obtained.

Base paste VA1 and catalyst paste B are mixed completely with one another in a weight ratio of 1,000 g VA1:140 g B. After some minutes, a rubber-elastic composition is obtained.

On the resulting cured composition, the permanent deformation of recovery after deformation of 1.4% and the deformation under pressure of 2.35% are measured in accordance with ISO 4823 (see also table 1).

Paste VA1 is stored at a constant temperature of 50° C. After periodic intervals, the viscosity is measured with a Haake viscometer. The viscosity exceeds 1,300 Pa.s after only one week (table 1).

Example 1

39.6 g of an aziridino-polyether which has been obtained according to example 12 of DE-B 17 45 810 are mixed with 23 g dibenzyltoluene, 17 g hydrogenated soya oil, 0.5 g of a block copolymer surfactant of propylene oxide and ethylene oxide having an average molecular weight of 4,400 and 17.8 g kieselguhr. After addition 2.1 g of a mixture of retardant, colored pigment and aroma, 100 g of a paste A1 are obtained.

Base paste A1 and catalyst paste B are mixed completely with one another in a weight ratio of 1,000 g A1:100 g B. After some minutes, a rubber-elastic composition is obtained.

On the resulting cured composition, the permanent deformation of recovery after deformation of 1.35% and the deformation under pressure of 2.65% are measured in accordance with ISO 4823 (see also table 1).

Paste A1 is stored at a constant temperature of 50° C. After periodic intervals, the viscosity is measured with a Haake viscometer. Even after two years, the viscosity remains below 1,000 Pa.s (table 1).

Comparison Example 2

39.6 g of an aziridino-polyether which has been obtained according to example 12 of DE-B 17 45 810 are mixed with 21.6 g dibenzyltoluene, 9.8 g hydrogenated beef tallow, 3.7 g of a block copolymer surfactant of propylene oxide and ethylene oxide having an average molecular weight of 4,400 and 23.6 g kieselguhr. After addition of 1.7 g of a mixture of retardant, coloured pigment and aroma, 100 g of a paste VA2 are obtained.

Base paste VA2 and catalyst paste B are mixed completely with one another in a weight ratio of 1,000 g VA2:100 g B. After some minutes, a rubber-elastic composition is obtained. On the resulting cured composition, the permanent deformation of recovery after deformation of 2.3% and the deformation under pressure of 3.9% are measured in accordance with ISO 4823 (see also table 1).

Paste VA2 is stored at a constant temperature of 50° C. After periodic intervals, the viscosity is measured with a Haake viscometer. The viscosity exceeds 1,300 Pa.s after only two weeks (table 1).

Preparation Example 2

(Esterification of a Fat in Itself)

100 g hydrogenated palm oil (e.g. PRIFAT 9835 from Unichema) are melted at 80° C., and 1.0 wt. % sodium methylate is added. The reaction mixture is stirred at 80° C. in vacuo for one hour and is then taken up in 300 ml toluene and extracted by shaking in each case once with dilute acetic acid and once with deionized water. After drying over sodium sulphate, the solvent is removed in vacuo and 97 g of palm oil esterified in itself are obtained.

Example 2

57.9 g of an aziridino-polyether which has been obtained according to example 12 of DE-B 17 45 810 are mixed with 11.6 g dibenzyltoluene, 11.6 g palm oil transesterified according to preparation example 2 (see above) and 16.3 g kieselguhr. After addition of 2.6 g of a mixture of retardant, coloured pigment and aroma, 10.0 g of a paste A2 are obtained.

Base paste A2 and catalyst paste B are mixed completely with one another in a weight ratio of 1,000 g A2:140 g B. After some minutes a rubber-elastic composition is obtained.

On the resulting cured composition, the permanent deformation of recovery after deformation of 1.25% and the deformation under pressure of 2.6% are measured in accordance with ISO 4823 (see also table 1).

Paste A2 is stored at a constant temperature of 50° C. After periodic intervals, the viscosity is measured with a Haake viscometer. Even after two years, the viscosity remains below 1,000 Pa.s (table 1).

Example 3

57.9 g of an aziridino-polyether which has been obtained according to example 12 of DE-B 17 45 810 are mixed with 11.6 g dibenzyltoluene, 11.6 g synthetic triacyl glyceride (SOFTISAN 154 Hüls) and 16.3 g kieselguhr. After addition of 2.6 g of a mixture of retardant, coloured pigment and aroma, 100 g of a paste A3 are obtained.

Base paste A3 and catalyst paste B are mixed completely with one another in a weight ratio of 1,000 g A3:140 g B. After some minutes, a rubber-elastic composition is obtained.

On the resulting cured composition, the permanent deformation of recovery after deformation of 1.5% and the deformation under pressure of 2.15% are measured in accordance with ISO 4823 (see also table 1).

Paste A3 is stored at a constant temperature of 50° C. After periodic intervals, the viscosity is measured with a Haake viscometer. Even after two years, the viscosity remains below 1,000 Pa.s (table 1).

Comparison Example 3

57.9 g of an aziridino-polyether which has been obtained according to example 12 of DE-B 17 45 810 are mixed with 11.6 g dibenzyltoluene, 11.6 g Dynasan P60 (Hüls) and 16.3 g kieselguhr. After addition of 2.6 g of a mixture of retardant, coloured pigment and aroma, 100 g of a paste VA3 are obtained.

Base paste VA3 and catalyst paste B are mixed completely with one another in a weight ratio of 1,000 g VA3:140 g B. After some minutes, a rubber-elastic composition is obtained.

On the resulting cured composition, the permanent deformation of recovery after deformation of 1.8% and the deformation under pressure of 3.25% are measured in accordance with ISO 4823 (see also table 1).

Paste VA3 is stored at a constant temperature of 50° C. After periodic intervals, the viscosity is measured with a Haake viscometer. The viscosity exceeds 1,300 Pa.s after only one week (table 1).

Comparison Example 4

57.9 g of an aziridino-polyether which has been obtained according to example 12 of DE-B 17 45 810 are mixed with 11.6 g dibenzyltoluene, 11.6 g hydrogenated beef tallow and 16.3 g kieselguhr. After addition of 2.6 g of a mixture of retardant, coloured pigment and aroma, 100 g of a paste VA4 are obtained.

Base paste VA4 and catalyst paste B are mixed completely with one another in a weight ratio of 1,000 g VA4:140 g B. After some minutes, a rubber-elastic composition is obtained.

On the resulting cured composition, the permanent deformation of recovery after deformation of 1.8% and the deformation under pressure of 2.6% are measured in accordance with ISO 4823 (see also table 1).

Paste VA4 is stored at a constant temperature of 50° C. After periodic intervals, the viscosity is measured with a Haake viscometer. The viscosity exceeds 1,300 Pa.s after only two weeks (table 1).

Example 4

39.6 g of an aziridino-polyether which has been obtained according to example 12 of DE-B 17 45 810 are mixed with 21.6 g dibenzyltoluene, 9.8 g hydrogenated soya oil, 3.7 g of a block copolymer surfactant of propylene oxide and ethylene oxide having an average molecular weight of 4,400 and 23.6 g kieselguhr. After addition of 1.7 g of a mixture of retardant, coloured pigment and aroma, 100 g of a paste A4 are obtained.

Base paste A4 and catalyst paste B are mixed completely with one another in a weight ratio of 1,000 g A4:100 g B. After some minutes, a rubber-elastic composition is obtained.

On the resulting cured composition, the permanent deformation of recovery after deformation of 1.4% and the deformation under pressure of 2.7% are measured in accordance with ISO 4823 (see also table 1).

Paste A4 is stored at a constant temperature of 50° C. After periodic intervals, the viscosity is measured with a Haake viscometer. Even after two years, the viscosity remains below 1,000 Pa.s (table 1).

Each of the publications referred to above is hereby incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

the impression composition; wherein the wt. % of (a) and (b) are based on the total weight of the composition.

2. The impression composition according to claim 1, which further comprises (c) about 10 to 65 wt. % of customary catalysts, auxiliaries or additives.

3. The impression composition according to claim 1, wherein component b) comprises a mixture of triacyl glycerides.

4. The impression composition according to claim 1, wherein component b) is a synthetic triacyl glyceride.

5. The impression composition according to claim 1, wherein the triacyl glyceride has the following formula

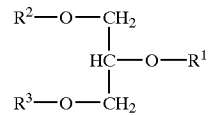

in which $R^1$, $R^2$, and $R^3$ independently of one another have the meaning $C_{11}H_{23}CO$, $C_{13}H_{27}CO$, $C_{15}H_{31}CO$ or $C_{17}H_{35}CO$, the proportion of $C_{17}H_{35}CO$ being distributed randomly among the radicals $R^1$, $R^2$ and $R^3$.

6. The impression composition according to claim 2, which comprises 30 to 40 wt. % of component (a), 5 to 20 wt. % of component (b), and 40 to 65 wt. % of component (c).

7. A ready-mixed impression composition based on vulcanizable polyether materials comprising, base components and a catalyst which are present in paste form spatially separate from one another, the base component comprising i) 30 to 75 wt. % aziridino-polyether, ii) 5 to 25 wt. % of a triacyl

TABLE 1

Mechanical properties and viscosity storage data of the polyether pastes

| | Comparison example 1 | Example 1 | Comparison example 2 | Example 2 | Example 3 | Comparison example 3 | Comparison example 4 | Example 4 |
|---|---|---|---|---|---|---|---|---|
| Base paste comprises | hyd. palm oil | hyd. soya oil | beef tallow | transest. palm oil | Softisan | Dynasan P 60 | beef tallow | hyd. soya oil |
| Aziridino-polyether [wt. %] | 57.9 | 39.6 | 39.6 | 57.9 | 57.9 | 57.9 | 57.9 | 39.6 |
| Thixotropic agent [wt. %] | 11.6 | 17 | 9.8 | 11.6 | 11.6 | 11.6 | 11.6 | 9.8 |
| Base:Cat. | 7:1 | 10:1 | 10:1 | 7:1 | 7:1 | 7:1 | 7:1 | 10:1 |
| PE content in the mixture [wt. %] | 50.79 | 36 | 36 | 50.79 | 50.79 | 50.79 | 50.79 | 36 |
| Thixotropic agent content in the mixture [wt. %] | 10.2 | 15.5 | 8.9 | 10.2 | 10.2 | 10.2 | 10.2 | 8.9 |
| Mech. properties | + | + | − | + | + | − | + | + |
| Permanent deformation [%] | 1.4 | 1.35 | 2.3 | 1.25 | 1.5 | 1.8 | 1.8 | 1.4 |
| Elastic deformation [%] | 2.35 | 2.65 | 3.9 | 2.6 | 2.15 | 3.25 | 2.6 | 2.7 |
| Storage stability (50° C.) | − | + | − | + | + | − | − | + |
| Time to viscosity > 1,300 Pa · s | 1 week | 2 years stable | 2 weeks | 2 years stable | 2 years stable | 1 week | 2 weeks | 2 years stable |

We claim:

1. A ready-mixed impression composition based on vulcanizable polyether materials comprising (a) about 30 to 70 wt. % of aziridino-polyether, and (b) about 5 to 20 wt. % of a triacyl glyceride of non-animal origin which has a random distribution of stearoyl radicals and a stearoyl content of <70 wt. % with no adverse influences on the storage stability of glyceride having a random distribution of stearoyl radicals and a stearoyl content of <70 wt. % with no adverse influences on the storage stability of the impression composition, and iii) 0 to 65 wt. % of customary auxiliaries and additives, and the catalyst component comprising iv) 10 to 60 wt. % of a customary catalyst, v) 0 to 25 wt. % of a triacyl glyceride according to component ii and vi) 15 to 90 wt. % of customary auxiliaries and additives, the wt. % data in each case being based on the total weight of the base paste and catalyst paste respectively.

8. A method of using triacyl glyceride to increase the storage time of a polyether-containing vulcanizable impression material, which comprises mixing an aziridino-polyether with a triacyl glyceride of non-animal origin which has a random distribution of stearoyl radicals and a stearoyl content of <70 wt. % with no adverse influences on the storage stability of the impression composition.

9. The ready-mixed impression composition according to claim 1, wherein the triacyl glyceride is hydrogenerated and is selected from the group consisting of avocado oil, cottonseed, oil, groundnut oil, cacao butter, pumpkin seed oil, linseed oil, maize germ oil, olive oil, palm oil, rice oil, rapeseed oils, safflower oil, sesame oil, soya oil, sunflower oil, grapeseed oil, wheatgerm oil, borneo tallow, fulwa tallow, hemp oil, illipé butter, lupin oil, candlenut oil, kapok oil, katiau fat, kenaf seed oil, kekuna oil, poppy oil, mowrah butter, okra oil, perilla oil, sal butter, shea butter and tung oil.

10. The method according to claim 8, wherein the triacyl glyceride is hydrogenated and is selected from the group consisting of avocado oil, cottonseed, oil, groundnut oil, cacao butter, pumpkin seed oil, linseed oil, maize germ oil, olive oil, palm oil, rice oil, rapeseed oils, safflower oil, sesame oil, soya oil, sunflower oil, grapeseed oil, wheatgerm oil, borneo tallow, fulwa tallow, hemp oil, illipé butter, lupin oil, candlenut oil, kapok oil, katiau fat, kenaf seed oil, kekuna oil, poppy oil, mowrah butter, okra oil, perilla oil, sal butter, shea butter and tung oil.

11. The ready-mixed impression composition according to claim 1, wherein the triacyl glyceride has an iodine number of less than 20.

12. The method according to claim 8, wherein the triacyl glyceride has an iodine number of less than 20.

13. The ready-mixed impression composition according to claim 1, wherein the triacyl glyceride is synthetic.

14. The method according to claim 8, wherein the triacyl glyceride is synthetic.

* * * * *